United States Patent [19]
Colvin

[11] Patent Number: 5,117,680
[45] Date of Patent: Jun. 2, 1992

[54] METHOD AND CONTROL CIRCUIT FOR MEASURING TRACE CONSTITUENTS IN AUTOMOTIVE ENGINE EXHAUST

[75] Inventor: Alex D. Colvin, Oak Park, Mich.

[73] Assignee: Ford Motor Company, Dearborn, Mich.

[21] Appl. No.: 727,038

[22] Filed: Jul. 8, 1991

Related U.S. Application Data

[63] Continuation-in-part of Ser. No. 633,925, Dec. 26, 1990.

[51] Int. Cl.⁵ .......................................... G01M 15/00
[52] U.S. Cl. ...................................... 73/116; 73/23.31
[58] Field of Search .................. 73/116, 23, 31, 31.05, 73/23.2; 204/406, 409, 411, 412, 415, 431, 228, 174

[56] References Cited

U.S. PATENT DOCUMENTS

| | | | |
|---|---|---|---|
| 3,473,372 | 10/1969 | Klink | 73/118 |
| 3,928,162 | 12/1975 | Takata | 204/195 |
| 4,029,563 | 6/1977 | Binder et al. | 252/408 |
| 4,277,368 | 7/1981 | Amy et al. | 254/408 |
| 4,321,056 | 3/1982 | Dimitroff | 23/230 |
| 4,391,690 | 7/1983 | Lin et al. | 204/412 |
| 4,409,069 | 10/1983 | Luft | 204/1 T |
| 4,499,190 | 2/1985 | Spicer et al. | 436/122 |
| 4,500,391 | 2/1985 | Schmidt et al. | 204/1 T |
| 4,532,023 | 7/1985 | Furst et al. | 204/409 |
| 4,622,105 | 11/1986 | Liu et al. | 204/1 T |
| 4,642,172 | 2/1987 | Fruhwald | 204/231 |
| 4,735,691 | 4/1988 | Green et al. | 204/1 T |

*Primary Examiner*—Robert Raevis
*Attorney, Agent, or Firm*—Peter Abolins; Roger L. May

[57] ABSTRACT

Provided is a method and circuit for measuring on a real-time basis trace constituents in vehicle engine exhaust. The control circuit operates to maintain a small, constant concentration of a selected electrolyte constituent reactive with the exhaust constituent sought to be measured. The amount of current necessary to regenerate and maintain the concentration of the selected electrolyte constituent is continuously measured to generate a real-time electrical signal proportional to the mass flow of the exhaust constituent entering the electrochemical cell.

32 Claims, 2 Drawing Sheets

METHOD AND CONTROL CIRCUIT FOR MEASURING TRACE CONSTITUENTS IN AUTOMOTIVE ENGINE EXHAUST

CROSS-REFERENCE TO RELATED APPLICATIONS

This application is a continuation-in-part of U.S. patent application Ser. No. 633,925 filed on Dec. 26, 1990, by Ford Motor Company. The applications, have at all relevant times hereto, been commonly owned.

TECHNICAL FIELD

This invention is related to a method and control circuit for measuring trace constituents in the flow of exhaust from vehicle engines. A circuit according to this invention is particularly well-suited for the measurement of engine oil consumption, as determined by the presence of combustion species attributable to chemical compounds contained in lubricating oil.

BACKGROUND ART

It is desirable for engine manufacturers to have a means for quickly determining engine oil consumption, because oil usage is important, not only for reasons of customer satisfaction, but also as a measure of basic engine integrity.

Many methods have been proposed for measurement of engine oil consumption. U.S. Pat. No. 3,473,372 to Klink discloses a system which uses a calibrated measuring vessel for determining oil usage. Such a system is hardly much of an improvement over the oldest known methods for measuring oil consumption in which the engine being tested was merely operated for an extended period of time sufficient to allow weighing or volume measurement techniques to determine, albeit with mediocre accuracy, the engine's oil consumption.

Engine designers have sought improved ways for measuring engine oil consumption for many years. One such alternative has involved the measurement of trace compounds in the engine exhaust. For example, a radiometric method involves the addition of a radioactive tracer to the oil, with the tracer being tracked in the engine's exhaust. This technique suffers from the drawback that it requires synthesis and addition of the radioisotope tagging compound, which renders the technique generally unsuitable for routine use.

Another method for determining engine oil usage involves the measurement of an oil additive, such as zinc dialkyldithiophosphate. Such a method is disclosed in U.S. Pat. No. 4,321,056 to Dimitroff. As disclosed by Dimitroff, a sample of the exhaust gas in the engine is passed through a condenser in order to condense zinc sulphate in the exhaust. After the sample is treated, it is passed through a coulometer cell wherein a reading is obtained which is proportional to the engine oil consumed during the sampling period. This system, unfortunately, is incapable of giving a real time measurement of engine oil consumption.

Electrochemical cells for measuring trace chemical constituents are also disclosed in U.S. Pat. Nos. 3,928,162 to Takata; 4,029,563 to Binder et al; 4,409,069 to Luft; and 4,622,105 to Liu et al. None of these cells is suitable for the continuous measurement of sulphur dioxide or any other trace element carried in the stream of exhaust coming from an engine, on a real-time basis.

U.S. Pat. No. 4,277,368 to Amy et al and U.S. Pat. No. 4,499,190 to Spicer et al disclose coulometric and fluorescent techniques for detecting sulphur dioxide. As with the previously noted coulometric methods, these methods are not suitable for measuring sulphur dioxide in a flowing exhaust stream from an engine in real-time because they lack adequate time response characteristics.

U.S. Pat. No. 4,500,391 to Schmidt discloses an electrochemical detection cell and circuitry capable of applying a fixed DC voltage bias to the reference electrode and superimposing a train of DC voltage pulses on the fixed bias. As disclosed by Schmidt, the circuitry functions to determine the difference between the sensing electrode signals. The difference is proportional to the concentration of the test gas in the atmosphere adjacent to the sensor.

U.S Pat. No. 4,735,691 to Green et al discloses an electrochemical detector cell consisting of two electrodes in which the cell is connected to an external current measurement circuit through a cyclically operated switch which alternately opens and closes a connection between the cell and the external cell. The cell is operated without bias potential. According to Green, by taking the difference between cell amplitudes, a differential current sample is provided which should be indicative of the cell current signal alone.

U.S. Pat. No. 4,642,172 to Fruhwald discloses a bias circuit adapted to be coupled with an electrochemical fuel cell for use in the detection of carbon monoxide or hydrogen sulfide.

SUMMARY OF THE INVENTION

The control circuit of the present invention operates to maintain a small, constant concentration of a selected electrolyte constituent in an electrochemical or coulometer cell. The electrolyte constituent is specifically chosen on the basis of its reactiveness with a selected exhaust constituent sought to be measured.

In operation, Applicant has found that the exhaust constituent reacts with and reduces the concentration of the electrolyte constituent in the electrochemical cell. Thus, by continuously measuring the amount of current necessary to regenerate and maintain the concentration of the electrolyte constituent, the mass flow of the exhaust constituent entering the cell may be determined on a real time basis.

For example, when measuring the amount of sulphur dioxide present in automotive engine exhaust, the control circuit of the present invention operates to maintain the concentration of iodine—a reactive electrolyte constituent—according to the following oxidation equation:

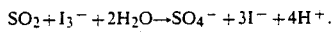

$$SO_2 + I_3^- + 2H_2O \rightarrow SO_4^- + 3I^- + 4H^+.$$

As seen from the equation, any sulfur dioxide ($SO_2$) present in the sample gas passing through the electrochemical cell will be oxidized. As a natural result, the iodine concentration will be significantly reduced. The amount of current necessary to produce sufficient iodine to maintain the iodine concentration in the cell is then measured and has been found to be coulometrically equal to the amount of sulfur dioxide entering the cell.

According to the present invention, a pair of detector electrodes are immersed in the electrochemical cell. The detector electrodes provide the circuit with a current signal that is directly proportional to the iodine concentration in the electrolyte solution. This signal is constantly compared with a reference signal which is commensurate with the desired iodine concentration. A difference signal is then generated based on the comparison to drive the reaction $$3I^- \rightarrow I_3^- + 2e^-.$$

This reaction, in turn, regenerates the used up iodine.

To minimize any nitrogen dioxide ($NO_2$) interference, PH buffers and potassium nitrite are added to the electrolyte solution.

OPERATION OF THE CIRCUIT

In operation, a small DC voltage is impressed between the two detector electrodes in the cell. The resultant current between the electrodes has been found to be proportional to the iodine concentration in the electrolyte solution.

The control circuit measures the current passing into the electrolyte solution from each electrode and further maintains the average electrode voltage between the electrodes so that no current passes from the iodine production anode—where any needed iodine is generated—to the detector electrodes.

Significantly, to prevent the flow of current from the iodine production anode to the detector electrodes, applicant has found that it is only necessary to make the two detector electrode currents equal in magnitude and opposite in direction. The circuit accomplishes this task by summing the two detector electrode current signals and providing a first output signal which, in turn, sets the average voltage on the detector electrodes. The difference between the two opposite detector electrode current signals is then measured and a second output signal is generated which is proportional to the iodine concentration in the electrolyte solution.

The second output signal is then compared with the desired iodine concentration or other reference value, and a third output signal is generated for input from the cathode to the iodine production anode. As disclosed by the applicant, the necessary iodine is produced at the production anode to regenerate and maintain the iodine concentration in the electrolyte solution. The current flowing between the cathode and the iodine production anode is then measured and a signal is generated which is a direct coulometric measurement of the sulphur dioxide entering the cell from the engine exhaust.

BEST MODE FOR CARRYING OUT THE INVENTION

Figure 1:
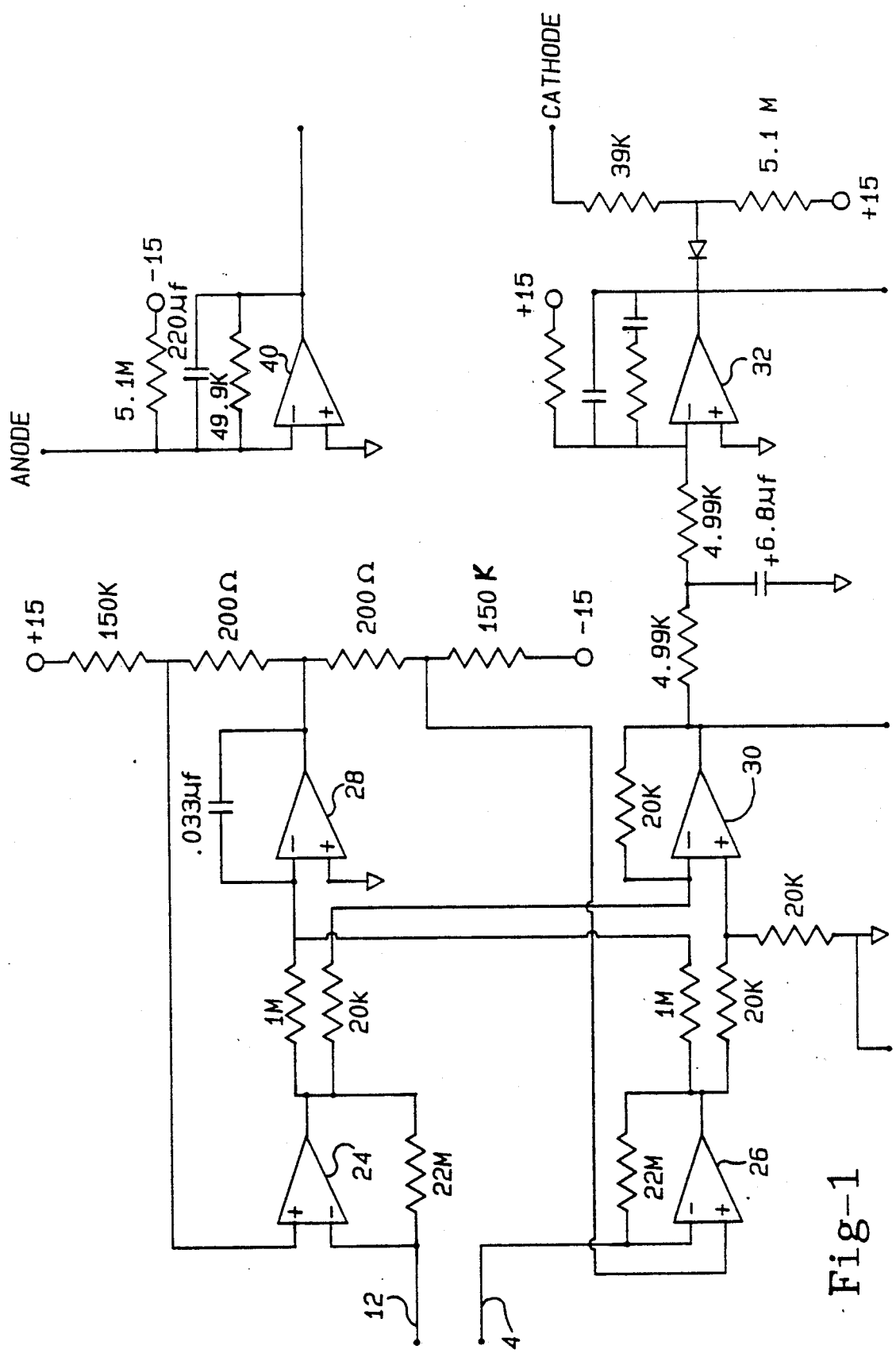
FIG. 1 is a detailed schematic diagram of the coulometer control circuit of the present invention.
Figure 2:
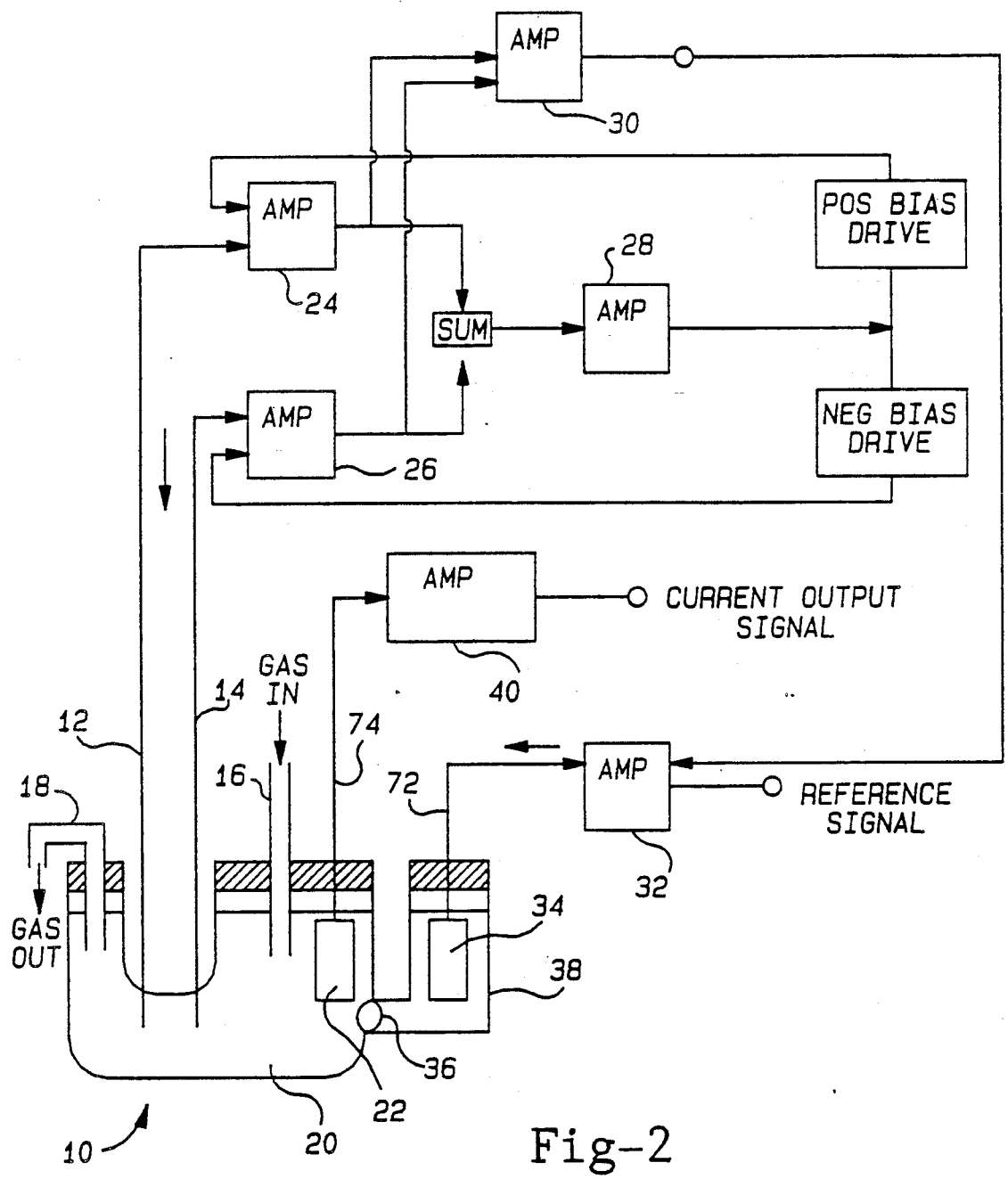
FIG. 2 is a block diagram of the coulometer control circuit of the present invention.

According to the invention described herein, there is provided an electrochemical or coulometric cell 10 and associated electronics. With reference to FIGS. 1 and 2, cell 10 is equipped with a pair of electrodes 12 and 14, respectively, which are preferably comprised of platinum. An inlet tube 16 and an outlet tube 18 are also provided for the sample gas to pass into and out of the cell while the trace constituents contained therein are measured.

The operation of the coulometer control circuit of the present invention will now be described as used to measure sulphur dioxide gas ($SO_2$) from a sample of automotive engine exhaust. In this application, it is recognized that the $SO_2$ constituent may be oxidized according to the following equation:

$$SO_2 + I_3^- + 2H_2O \rightarrow SO_4^- + 3I^- + 4H+.$$

Potassium iodide (KI) is therefore added to the electrolyte solution 20. In operation, electrodes 12 and 14 continuously provide a current signal that is directly proportional to the iodine concentration in the electrolyte solution 20.

As shown in FIG. 2, electrodes 12 and 14 are immersed in the electrolyte solution 20 and a small DC voltage on the order of 40 millivolts is impressed therebetween. The resultant current between the electrodes has been found by Applicant to be proportional to the iodine concentration in the electrolyte solution.

Still referring to FIG. 2, the control circuit of the present invention maintains the voltage between the electrodes 12 and 14, measures the current passing into the electrolyte solution 20 from each electrode and maintains the average electrode voltage so that no current passes from the iodine production anode 22, where any needed iodine is generated, to the detector electrodes 12 and 14.

To prevent the flow of current from the iodine production anode 22 to the detector electrodes 12 and 14, Applicant has found that it is only necessary to make the detector electrode currents equal in magnitude and opposite in direction. The circuit accomplishes this task by measuring the current passing into the electrolyte solution 20 from each electrode using current-to-voltage amplifiers 24 and 26 and summing the signals in an integrator 28.

More specifically, current-to-voltage amplifier 24 is placed in electrical contact with detector electrode 12 and generates a first electrical signal which corresponds to the sum of the electrolyte solution voltage and the voltage generated by current flowing through detector electrode 12. Similarly, current-to-voltage amplifier 26 is placed in electrical contact with detector electrode 14 and generates a second electrical signal which corresponds to the difference of the electrolyte solution voltage and the voltage generated by current flowing through detector electrode 14. These first and second electrical signals are then summed by integrator 28 which is placed in electrical contact with current-to-voltage amplifiers 24 and 26. Integrator 28 generates a third electrical signal which corresponds to the average voltage of the first and second electrical signals and further drives detector electrodes 12 and 14 while maintaining the average voltage between so that no current passes from the iodine production anode 22 to the detector electrodes 12 or 14. Integrator 28 is preferably an average bias drive amplifier.

Referring now to FIGS. 1 and 2, it can be seen that by setting the average voltage on the detector electrodes 12 and 14, amplifiers 24 and 26 act as current-to-voltage converters. If the current passing through electrodes 12 and 14 is not equal, then the output of the average bias drive integrator 28 is non-zero. Accordingly, an appropriate offset occurs on the reference inputs to amplifiers 24 and 26 which will equalize the current. In this manner, any potential drop between electrodes 12 and 14, other than the 40 millivolts, is compensated for.

In operation, applicant's coulometer control circuit assures that there are no stray currents in the cell which are unrelated to the iodine concentration in the electrolyte solution 20.

Still referring to FIGS. 1 and 2, Applicant discloses the use of a difference amplifier 30 which compares the outputs of amplifiers 24 and 26, with the difference being proportional to the detector current flowing between electrodes 12 and 14 and further proportional to the iodine concentration in the electrolyte solution.

Amplifier 30 generates a current for input to amplifier 32 that is proportional to the difference between the outputs of amplifier 24 and amplifier 26. Amplifier 32 then compares the output of amplifier 30 with the desired iodine concentration or other reference value.

If the current of amplifier 30 is less than the reference value, then the difference is used to produce a current through cell 10 from cathode 34 to iodine production anode 22. As shown in FIG. 2, a frit 36 is also positioned in the cell arm 38 which permits the transfer of ions but not solution.

Iodine in the cell is produced according to the following equation:

$$3I^- \rightarrow I_3 + 2e^-$$

Finally, the current needed to generate and maintain a constant concentration of iodine in the electrolyte solution is then measured in a current-to-voltage amplifier 40. Applicant has found that the disclosed method and circuit will generate just enough iodine ($I_3^-$) to make up for the iodine used up according to the oxidation equation above. This current is also directly related to, and therefore a measure of, the sulphur dioxide ($SO_2$) entering the cell from the automotive engine exhaust.

While the best mode for carrying out the invention has been described in detail, those familiar with the art to which this invention relates will recognize various alternative designs and embodiments for practicing the invention as defined by the following claims.

I claim:

1. For use in continuously measuring on a real-time basis the mass flow of a sample constituent of vehicle engine exhaust, a control arrangement, comprising:
    an electrochemical cell having an electrolyte solution adapted to receive the sample constituent;
    a pair of detector electrodes in electrical contact with said electrolyte solution;
    a cathode in electrical contact with said electrolyte solution;
    an anode in electrical contact with said electrolyte solution for receiving current from said cathode and producing a selected electrolyte constituent reactive with the sample gas constituent in said electrolyte solution;
    voltage generating means for generating a selected voltage between said detector electrodes to maintain the average voltage therebetween so that no current passes from said anode to said detector electrodes;
    first signal generating means for generating a first electrical signal proportional to the current between said detector electrodes and further proportional to the concentration of said selected electrolyte constituent in said electrolyte solution;
    second signal generating means for receiving and comparing said first electrical signal to a predetermined reference value corresponding to the desired concentration of said selected electrolyte constituent in said electrolyte solution and generating a second electrical signal for input from said cathode to said anode to produce sufficient amounts of said selected electrolyte constituent so as to maintain a constant concentration of said selected electrolyte constituent in said electrolyte solution of said electrochemical cell; and
    third signal generating means for measuring current between said cathode and said anode and generating a third electrical signal proportional to the mass flow of the sample constituent entering the electrochemical cell on a real-time basis.

2. A control circuit for continuously measuring on a real-time basis the mass flow of a sample constituent of vehicle engine exhaust introduced into the electrolyte solution of an electrochemical cell, comprising:
    a pair of detector electrodes in electrical contact with the electrolyte solution;
    a cathode in electrical contact with the electrolyte solution;
    an anode in electrical contact with the electrolyte solution for receiving current from said cathode and producing a selected electrolyte constituent reactive with the sample gas constituent in the electrolyte solution;
    voltage generating means for generating a selected voltage between said detector electrodes to maintain the average voltage therebetween so that no current passes from said anode to said detector electrodes;
    first signal generating means for generating a first electrical signal proportional to the current between said detector electrodes and further proportional to the concentration of said selected electrolyte constituent in the electrolyte solution;
    second signal generating means for receiving and comparing said first electrical signal to a predetermined reference value corresponding to the desired concentration of said selected electrolyte constituent in the electrolyte solution and generating a second electrical signal for input from said cathode to said anode to produce sufficient amounts of said selected electrolyte constituent so as to maintain a constant concentration of said selected electrolyte constituent in the electrolyte solution of the electrochemical cell; and
    third signal generating means for measuring current between said cathode and said anode and generating a third electrical signal proportional to the mass flow of the sample constituent entering the electrochemical cell on a real-time basis.

3. A control circuit as in claim 2 wherein said pair of detector electrodes comprises a first detector electrode in electrical contact with the electrolyte solution and a second detector electrode in electrical contact with the electrolyte solution.

4. A control circuit as in claim 3 wherein said voltage generating means further comprises:
    a fourth signal generating means in electrical contact with said first detector electrode for generating a fourth electrical signal, said fourth electrical signal corresponding to the sum of the electrolyte solution voltage and the voltage generated by current flowing through said first detector electrode; and
    a fifth signal generating means in electrical contact with said second detector electrode for generating a fifth electrical signal, said fifth electrical signal corresponding to the difference of the electrolyte solution voltage and the voltage generated by current flowing through said second detector electrode.

5. A control circuit as in claim 4 wherein said fourth signal generating means comprises a current-to-voltage amplifier.

6. A control circuit as in claim 4 wherein said fifth signal generating means comprises a current-to-voltage amplifier.

7. A control circuit as in claim 2 wherein said voltage generating means comprises a voltage integrator amplifier.

8. A control circuit as in claim 2 wherein said first signal generating means comprises a difference amplifier.

9. A control circuit as in claim 2 wherein said second signal generating means comprises a current driver amplifier.

10. A control circuit as in claim 2 wherein said third signal generating means comprises a current-to-voltage converter amplifier.

11. A control circuit as in claim 2 wherein said pair of detector electrodes comprises a pair of platinum wires.

12. A control circuit for continuously measuring on a real-time basis the mass flow of a sample constituent of vehicle engine exhaust introduced into the electrolyte solution of an electro-chemical cell, comprising:

a first detector electrode in electrical contact with the electrolyte solution;

a second detector electrode in electrical contact with the electrolyte solution;

a cathode in electrical contact with the electrolyte solution;

an anode in electrical contact with the electrolyte solution for receiving current from said cathode and producing a selected electrolyte constituent reactive with the sample gas constituent in the electrolyte solution;

a first signal generating means in electrical contact with said first detector electrode for generating a first electrical signal corresponding to the sum of the electrolyte solution voltage and the voltage generated by current flowing through said first detector electrode;

a second signal generating means in electrical contact with said second detector electrode for generating a second electrical signal corresponding to the difference of the electrolyte solution voltage and the voltage generated by current flowing through said second detector electrode;

a third signal generating means in electrical contact with said first and second signal generating means for receiving said first and second electrical signals and generating a third electrical signal corresponding to the average voltage of said first and second electrical signals to drive said first and second detector electrodes and maintain the average voltage therebetween so that no current passes from said anode to said first or second detector electrodes;

a fourth signal generating means in electrical contact with said first and second signal generating means for receiving said first and second electrical signals and generating a fourth electrical signal corresponding to the voltage difference between said first and second electrical signals, said fourth electrical signal proportional to the current between said first and second detector electrodes;

a fifth signal generating means for receiving said fourth electrical signal and generating a fifth electrical signal from said cathode to said anode to produce sufficient amounts of said selected electrolyte constituent so as to maintain a constant concentration of said selected electrolyte constituent in the electrochemical cell; and a sixth signal generating means in electrical contact with the electrolyte solution for measuring current between said cathode and said anode and generating a sixth electrical signal proportional to said current and further proportional to the mass flow of the sample gas constituent entering the electrochemical cell on a real-time basis.

13. A control circuit as in claim 12 wherein in said first signal generating means comprises a current-to-voltage amplifier.

14. A control circuit as in claim 12 wherein said second signal generating means comprises a current-to-voltage amplifier.

15. A control circuit as in claim 12 wherein said third signal generating means comprises a voltage integrator amplifier.

16. A control circuit as in claim 12 wherein said fourth signal generating means comprises a differential amplifier.

17. A control circuit as in claim 12 wherein said fifth signal generating means comprises a current driver amplifier.

18. A control circuit as in claim 12 wherein said sixth signal generating means comprises a current-to-voltage converter amplifier.

19. A control circuit as in claim 12 wherein said first detector electrode comprises a platinum wire.

20. A control circuit as in claim 12 wherein said second detector electrode comprises a platinum wire.

21. A control circuit for continuously measuring on a real-time basis the mass flow of the sulphur dioxide constituent of vehicle engine exhaust introduced into the electrolyte solution of an electrochemical cell, comprising:

a first detector electrode in electrical contact with the electrolyte solution;

a second detector electrode in electrical contact with the electrolyte solution;

a cathode in electrical contact with the electrolyte solution;

an anode in electrical contact with the electrolyte solution for producing iodine in the electrolyte solution;

a first signal generating means in electrical contact with said first detector electrode for generating a first electrical signal corresponding to the sum of the electrolyte solution voltage and the voltage generated from current flowing through said first detector electrode;

a second signal generating means in electrical contact with said second detector electrode for generating a second electrical signal corresponding to the difference of the electrolyte solution voltage and the voltage generated from current flowing through said second detector electrode;

a third signal generating means in electrical contact with said first and second signal generating means for receiving said first and second electrical signals and generating a third electrical signal corresponding to the average voltage of said first and second electrical signals to drive said first and second detector electrodes and maintain the average voltage therebetween so that no current passes from said anode to said first or second detector electrodes;

a fourth signal generating means in electrical contact with said first and second signal generating means for receiving said first and second electrical signals and generating a fourth electrical signal corresponding to the voltage difference between said first and second electrical signals, said fourth electrical signal proportional to the current between said first and second detector electrodes;

a fifth signal generating means for receiving said fourth electrical signal and generating a fifth electrical signal from said cathode to said anode to produce sufficient amounts of iodine so as to maintain a constant concentration of iodine in the electrolyte solution of the electrochemical cell;

a sixth signal generating means in electrical contact with the electrolyte solution for measuring current between said cathode and said anode and generating a sixth electrical signal proportional to said current and further proportional to the mass flow of sulphur dioxide in the automotive engine exhaust entering the electrochemical cell on a real-time basis.

22. A control circuit as in claim 21 wherein said first signal generating means comprises a current-to-voltage amplifier.

23. A control circuit as in claim 21 wherein said second signal generating means comprises a current-to-voltage amplifier.

24. A control circuit as in claim 21 wherein said third signal generating means comprises a voltage integrator amplifier.

25. A control circuit as in claim 21 wherein said fourth signal generating means comprises a differential amplifier.

26. A control circuit as in claim 21 wherein said fifth signal generating means comprises a current driver amplifier.

27. A control circuit as in claim 21 wherein said sixth signal generating means comprises a current-to-voltage converter amplifier.

28. A control circuit as in claim 21 wherein said first detector electrode comprises a platinum wire.

29. A control circuit as in claim 21 wherein said second detector electrode comprises a platinum wire.

30. A method for continuously measuring on a real-time basis the mass flow of the sulphur dioxide constituent of vehicle engine exhaust introduced into the electrolyte solution of an electrochemical cell, comprising the steps of:
providing a first detector electrode in electrical contact with the electrolyte solution;
providing a second detector electrode in electrical contact with the electrolyte solution;
providing a cathode in electrical contact with the electrolyte solution;
providing an anode in electrical contact with the electrolyte solution for producing iodine;
generating a first electrical signal corresponding to the sum of the electrolyte solution voltage and the voltage generated by current flowing through said first detector electrode;
generating a second electrical signal corresponding to the difference of the electrolyte solution voltage and the voltage generated by current flowing through said second detector electrode;
generating a third electrical signal corresponding to the average voltage of said first and second electrical signals to drive said first and second detector electrodes and maintain the average voltage therebetween so that no current passes from said anode to said first or second detector electrodes;
generating a fourth electrical signal corresponding to the difference between said first and second electrical signals, said fourth electrical signal proportional to the current between said first and second detector electrodes and further proportional to the concentration of the iodine concentration in the electrolyte solution;
comparing said fourth electrical signal with a predetermined reference value corresponding to the desired concentration of iodine in the electrolyte solution;
generating a fifth electrical signal for input from said cathode to said anode to produce sufficient amounts of iodine so as to maintain a constant concentration of iodine in the electrolyte solution;
measuring the current between said cathode and said anode; and
generating a real-time electrical signal proportional to the current between said cathode and said anode, said real-time electrical signal further proportional to the mass flow of sulphur dioxide in the automotive engine exhaust.

31. A method for continuously measuring on a real-time basis the mass flow of a sample constituent of vehicle engine exhaust introduced into the electrolyte solution of an electrochemical cell having a cathode, an anode, and a pair of detector electrodes all in electrical contact with the electrolyte solution, said electrolyte solution containing a selected constituent reactive with the sample constituent being measured, comprising the steps of:
impressing a selected voltage between the detector electrodes to maintain the average voltage therebetween so that no current passes from the anode to the detector electrodes;
generating a first electrical signal proportional to the current between the detector electrodes and further proportional to the concentration of the selected electrolyte constituent in the electrolyte solution;
comparing said first electrical signal to a predetermined reference value corresponding to the desired concentration of the selected electrolyte constituent;
generating a second electrical signal for input from the cathode to the production anode to produce sufficient amounts of the selected electrolyte constituent so as to maintain a constant concentration of the selected electrolyte constituent in the electrolyte solution;
measuring the current between said cathode and said anode; and
generating a real-time electrical signal proportional to the current between the cathode and anode and further proportional to the mass flow of the sample gas constituent being measured.

32. A control circuit for continuously measuring on a real-time basis the mass flow of a sample constituent of vehicle engine exhaust in, a control arrangement, comprising:
an electrochemical cell having an electrolyte solution adapted to receive the sample constituent;

a pair of detector electrodes in electrical contact with said electrolyte solution;

a cathode in electrical contact with said electrolyte solution;

an anode in electrical contact with said electrolyte solution for receiving current from said cathode and producing a selected electrolyte constituent reactive with the sample gas constituent in said electrolyte solution;

voltage generating means for generating a selected voltage between said detector electrodes to maintain the average voltage therebetween so that no current passes from said anode to said detector electrodes;

first signal generating means for generating a first electrical signal proportional to the current between said detector electrodes and further proportional to the concentration of said selected electrolyte constituent in the electrolyte solution;

second signal generating means for receiving and comparing said first electrical signal to a predetermined reference value corresponding to the desired concentration of said selected electrolyte constituent in the electrolyte solution and generating a second electrical signal for input from said cathode to said anode to produce sufficient amounts of iodine so as to maintain a constant concentration of iodine in the electrolyte solution of the electrochemical cell; and third signal generating means for measuring current between said cathode and said anode and generating a third electrical signal proportional to the mass flow of the sample gas constituent entering the electrochemical cell on a real-time basis.

* * * * *